United States Patent [19]

Tsugita et al.

[11] Patent Number: 4,865,994
[45] Date of Patent: Sep. 12, 1989

[54] DETECTION METHOD FOR AMINO ACID DERIVATIVES

[75] Inventors: Akira Tsugita, Suita; Isamu Arai, Fussa; Tatsuaki Ataka, Tokyo, all of Japan

[73] Assignee: Seiko Instruments & Electronics Ltd., Tokyo, Japan

[21] Appl. No.: 185,324

[22] Filed: Apr. 19, 1988

Related U.S. Application Data

[63] Continuation of Ser. No. 865,076, May 19, 1986, abandoned.

[30] Foreign Application Priority Data

May 17, 1985 [JP] Japan .................. 60-105400

[51] Int. Cl.$^4$ ...................... G01N 33/60; G01N 33/68
[52] U.S. Cl. ........................... 436/57; 436/89; 436/92; 436/172
[58] Field of Search .................. 436/57, 89, 92, 172

[56] References Cited

U.S. PATENT DOCUMENTS 3,645,689  2/1972  Sjoquist .
4,065,412  12/1977  Dreyer ..................... 422/129 X
4,153,416  5/1979  Bonner et al. .............. 436/57

FOREIGN PATENT DOCUMENTS 0202894  11/1986  European Pat. Off. .......... 436/86
110955   8/1980   Japan ..................... 436/89
182145   11/1982  Japan ..................... 436/89

OTHER PUBLICATIONS

Edman et al., Encyclopedia Biochem., 1 (1007), 20-01.
D. G. Klapper, "Trends in Automated Protein Sequence Analysis," Trac:Trends in Analytical Chemistry, vol. 2, No. 12, Dec. 1983, pp. 267-269.

Primary Examiner—Barry S. Richman
Assistant Examiner—Jill Johnston
Attorney, Agent, or Firm—Bruce L. Adams; Van C. Wilks

[57] ABSTRACT

A method for detecting amino acid derivatives in which 2-anilino-5-thiazolinone derivatives of amino acids are reacted with radioactive iodine siotope-labeled amino compounds or with fluorescent amino compounds to form phenylthiocarbamyl amino acid derivatives. The phenylthiocarbamyl amino acid derivatives are detected with a high level of sensitivity by a radioactive detector or a fluorescence spectrophotometer.

8 Claims, 5 Drawing Sheets

PROCESS FLOWSHEET OF PRIOR ART METHOD (i)

(ii)

(iii)

(i)

(ii)

DETECTION METHOD FOR AMINO ACID DERIVATIVES

This is a Rule 62 continuation application of parent application Ser. No. 865,076, filed May 19, 1986, now abandoned.

BACKGROUND OF THE INVENTION

1. Field of the Invention

This invention relates to a method for detecting amino acids for application to sequence determination from the amino (N) terminal of a protein. More particularly, it relates to a method for detecting amino acids with high sensitivity by using an amino compound containing a radioactive iodine isotope, for example, iodohistamine or a fluorescent amino compound, for example, aminopyrene or aminofluorene.

2. Description of the Prior Art

For the detection of amino acids in the final step of the phenylisothiocyanate method according to Edmon, P., Acta. Chem. Scand. 10 761 (1956), which is an N-terminal sequence determination method, it has been a usual practice as shown in FIG. 2 that thiazolinone derivatives are treated with an acid to form phenylthiohydantoin (PTH) derivatives and these derivatives are determined spectrophotometrically.

Although the prior art method for spectrophotometrically detecting PTH derivatives is simple and convenient as detection means, it cannot fully cope with a recent trend toward more highly sensitive analysis of a protein with a smaller amount of specimen.

For the high sensitivity detection of amino acids, methods of using $^{32}S$ PITC labelling or $^{135}I$ PITC labelling are shown in the following publication, PITC standing for phenylisothiocyanate:

W. G. Lauer, *Fundamental Techniques in Virology*, Eds. K. Habel and N. P. Salgman p. 379 (1969) Academic Press N.Y.

C. J. Burrell, P. D. Cooper, J. M. Swann, Aust J. Chem. 28 2289, (1975).

In above methods, radioactive isotope derivatives take part in the main reaction in the Edman degradation method. If high radioactivity is used for the purpose of realizing high sensitivity, not only radioactive disintegration increases, which adversely affects a yield itself in the Edman amino acid sequence determination, but also the contamination of the environment occurs.

SUMMARY OF THE INVENTION

The present inventive method comprises reacting thiazolinone derivatives with a radioactive isotope labelled amine compound or fluorescent amino compound to form phenylthiocarbamyl amino acid derivatives and detecting these amino acid derivatives with high sensitivity by means of a radioactivity detector or a fluorescence spectrophotometer.

Therefore, it is an object of this invention to provide a novel method for detecting amino acids with higher sensitivity.

BRIEF DESCRIPTION OF THE DRAWINGS

FIG. 3 (i): just after mixing

FIG. 3 (ii): after heating at 50° C. for 30 min

FIG. 3 (iii): after heating at 50° C. for one hour
(a) thiazoline derivative of leucine
(b) phenylthiocarbamyl (PTC) derivative of leucine

DETAILED DESCRIPTION OF THE INVENTION

Figure 1:
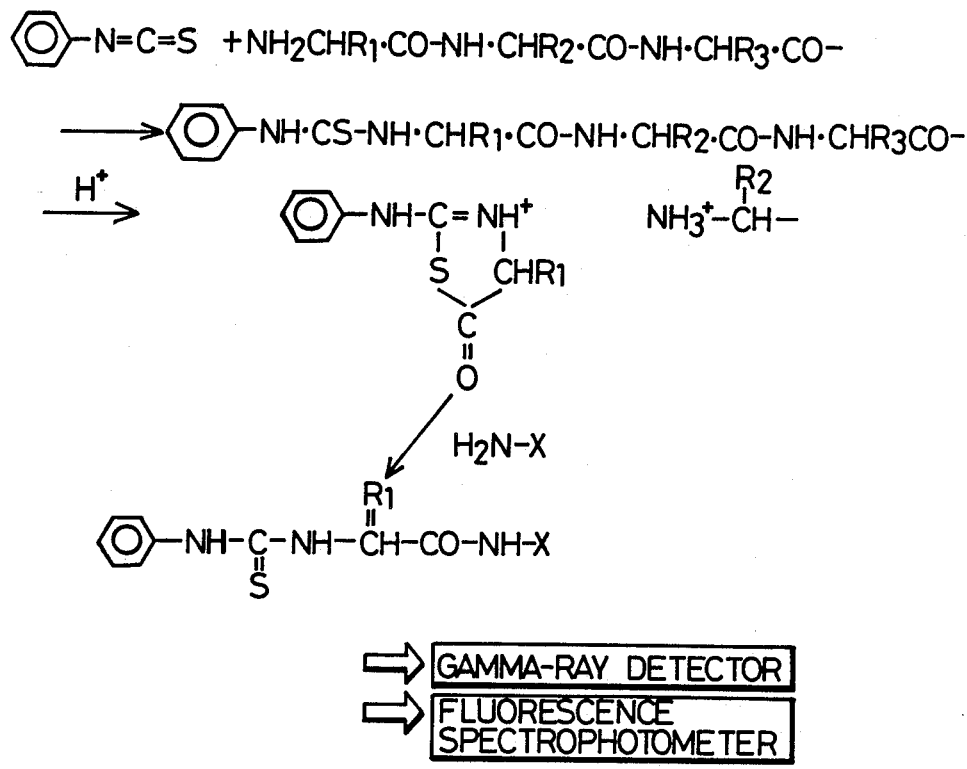
FIG. 1 is a process flowsheet showing the detection method of this invention.
Figure 2:
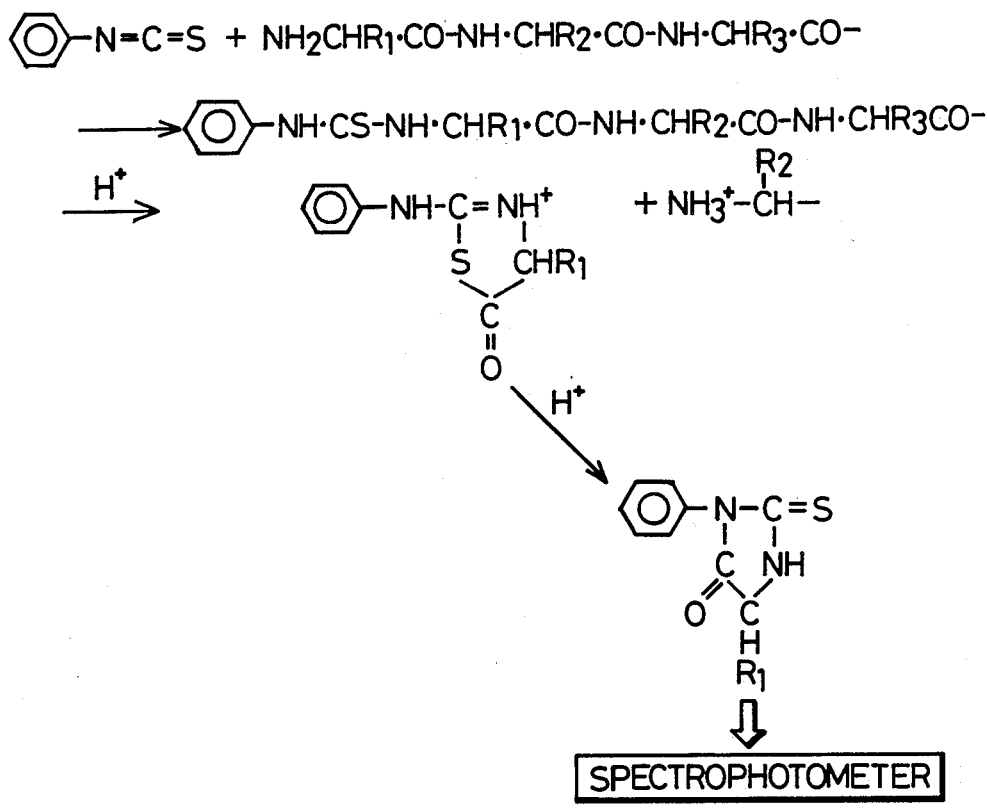
FIG. 2 is a process flowsheet of a prior art method.

This invention will now be described in more detail with reference to examples.

EXAMPLE 1

This example demonstrates a basic detection method wherein 5-thiazolinone derivatives of amino acids (ATZ) were reacted with a radioactive iodine isotope-labelled iodohistamine to form phenylthiocarbamyl amino acid derivatives and these products were detected with high sensitivity.

This method will be described in the following order. Hereinbelow, a dipeptide (Leu-Ala) consisting of leucine (Leu) and alanine (Ala) is used instead of a protein for simplicity.

1. PTC-Leu-Ala and ATZ-Leu
   (i) synthesis of PTC-Leu-Ala
   (ii) synthesis and purification of ATZ-Leu
2. coupling reaction
3. detection of phenylthiocarbamyl amino acid derivatives 1. PTC-Leu Ala and ATZ-Leu
   (i) synthesis of PITC-Leu-Ala

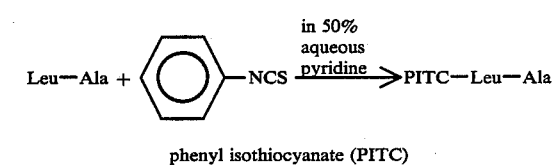

phenyl isothiocyanate (PITC)

Leu-Ala (202 mg) was dissolved in 50% aqueous pyridine, and the pH was adjusted to 8.6 by the addition of 2N NaOH. Subsequently, PITC was added thereto. The pH was kept at 8.6 by the addition of 2N NaOH because it was decreasing with the addition of PITC. After the variation in the pH had been stopped, the solution was heated at 40° C. for one hour. After the reaction, the reaction solution was washed with benzene. After the benzene dissolved in the water phase had been purged with $N_2$ gas, the pH was adjusted to 2 by the addition of 1N HCl, whereupon PTC-Leu-Ala was obtained in the form of a white precipitate.

Yield: 270 mg, % yield: 80%, m.p.: 148° C.

(ii) synthesis and purification of ATZ-Leu

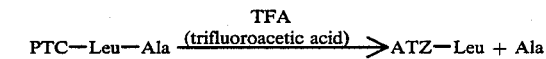

The above PITC-Leu-Ala (100 mg) was dissolved in TFA (1 ml), and the solution was heated at 50° C. for 5 min. After the reaction, the solution was evaporated to dryness. Butyl chloride was added to the residue to thoroughly dissolve the product in it, and the resulting solution was passed through a cellulose column (Ala was adsorbed on the column). The effluent was collected and evaporated to dryness. ATZ-Leu was obtained in the form of a white solid.

Yield: 70 mg, % yield: 95%.

2. coupling reaction

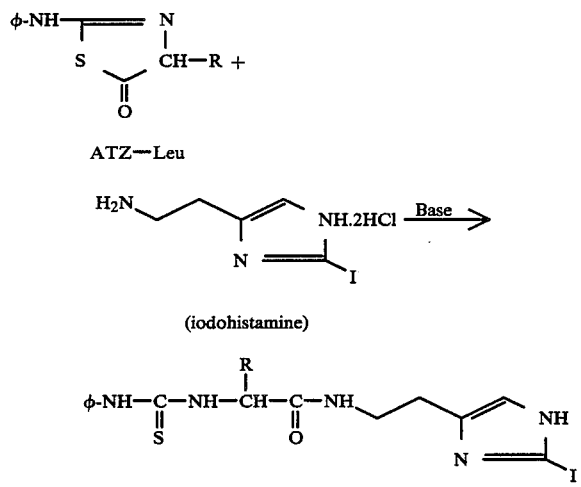

ATZ—Leu

As the above reaction formula shows the amino group of iodohistamine attacks the carbonyl group of ATZ amino acid to give a product. The reaction is the reverse of a reaction for cleaving the peptide bond between PTC amino acid and the peptide.

ATZ-Leu (70 mg) obtained from PTC-Leu-Ala was dissolved in 30% pyridine/dimethylformamide (20 ml), to which was then added iodohistamine 2HCl (200 mg), the resulting mixture was heated with agitation at 50° C. for one hour. The reaction solution was evaporated to dryness and the residue was dried to solid and extracted with 1M sodium bicarbonate and ethyl acetate. The ethyl acetate phase was dried and evaporated to dryness. The residue was recrystallized from benzene to obtain a product in the form of a white crystal.

Yield: 120 mg, % yield: 83%.

There was good agreement between the results by elementary analysis of this product and the values calculated from its theoretical formula.

3. detection of phenylthiocarbamyl amino acid derivatives

Figure 3:
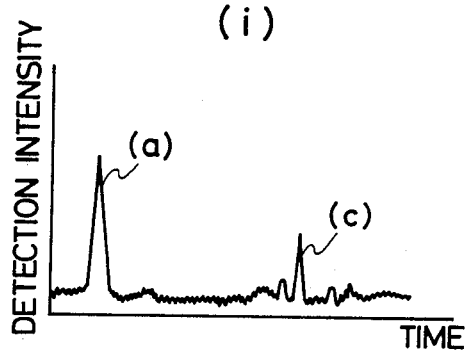
FIG. 3 are HPLC charts of a reaction mixture and a reaction product (mixing or reaction between ATZ-Leu (the anilinothiazolinone derivative of leucine) and iodohistamine).
Figure 3:
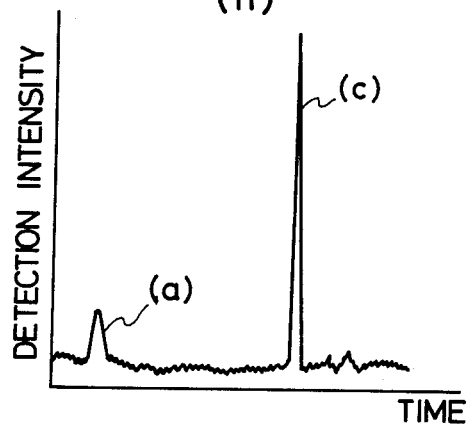
Figure 3:
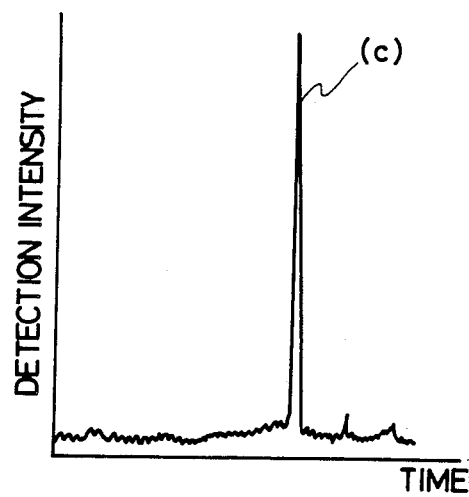

The reaction mixture including the reaction product was chromatographed by high-pressure liquid chromatography (HPLC) and the detection was made by ultraviolet spectra (at 269 nm). The results are shown in FIG. 3. FIG. 3 (i) shows an HPLC chromatogram just after mixing, FIG. 3 (ii) shows an HPLC chart after heating at 50° C. for 30 min, and FIG. 3 (iii) shows an HPLC chart after heating at 50° C. for one hour. As these figures clearly show, the coupling reaction between the thiazolinone derivative of leucine and iodohistamine was completed by heating at 50° C. for one hour, so that the thiazolinone derivative was detected in the form of a PTC leucine derivative.

(conditions of HPLC)

column:
SERVA Cat. No. 4231
250 mm×4.6 mm
SERVACHROM Packing (SERVACHROM is a tradename of SERVA FEINBIOCHAMICA GmbH for high pressure liquid chromatography columns)
S:100:polyol:RP18
5 μm solvent system:

| buffer solution | organic solvent |
|---|---|
| 0.015 M NaOAc (pH = 5 with AcOH) | CH$_3$CN—MeOH |
| 1 | (4:1) 5 | effluent flow rate: 1.5 ml/min
detection: 269 nm
chart speed: 10 mm/min
NaOAc=sodium acetate; AcOH=acetic acid

EXAMPLE 2

This example demonstrates one wherein a method similar to that described in Example 1 was applied to various dipeptides and a pentapeptide, and the detection was performed by using thin-layer chromatography and an X-ray film.

The dipeptides and pentapeptide used were as follows: Leu-Gly, Pro-Phe, Phe-Ala, Met-Leu, Ser-Phe, Ile-Ser, Gly-Glu, Ala-Ala, Val-Glu, Gln-Gly, and Tyr-Gly-Gly-Phe-Leu.

A similar method to that described in Example 1 was followed. Namely, each of the above peptides was reacted with phenyl isothiocyanate (PITC) to form a phenylthiocarbamyl peptide, which was converted into a thiazolinone derivative by cyclization and scission by treatment with trifluoroacetic acid. This thiazolinone derivative was reacted with iodohistamine labelled with a radioactive isotope to form a phenylthiocarbamylamino acid derivative. A variety of the formed phenylthiocarbamyl amino acid derivatives were developed on a thin-layer chromatogram and then detected as clear exposed spots on an X-ray film after exposure for several hours. In the thin-layer chromatography, a solvent system comprising benzene, methanol and tert-butyl alcohol in a volume ratio of 8:1:1 was used in development.

Figure 4:
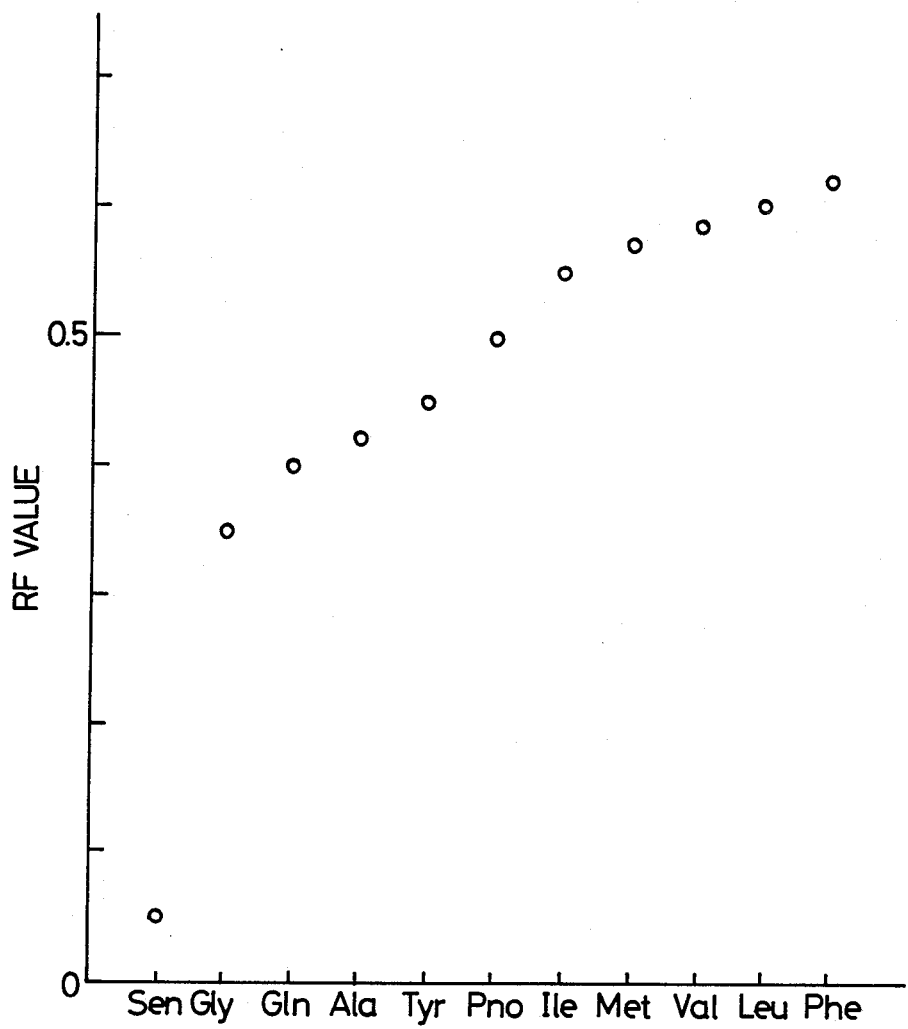
FIG. 4 is a thin-layer chromatogram of various iodohistamine derivatives of PTC amino acids.

The results are shown in FIG. 4, wherein ordinates represent RF (retention factor) values. As compared with the sensitivity of detection of the prior art, that of this invention was extremely high as follows:

| detection method | sensitivity of detection |
|---|---|
| (prior art) phenylthiohydantoinamino acid method | ~10 pico mole |
| this invention | 01 ~ 10 femto mole |

In this Example, no radioactive substance is used in the main reaction, though it is used in only the final step in the sequence determination method, so that the main reaction is quite the same as in the prior art and a radioactive substance is used in a special vessel in only the final modification reaction of a reaction product intermediate (ATZ) in each step and therefore the reaction itself does not differ at all from that in the prior art. Therefore, it is possible to perform the reaction without adversely affecting the reaction yield while minimizing radioactive contamination.

EXAMPLE 3

This example demonstrates wherein 5-anilino 5-thiazolinone derivatives of amino acids were reacted with a fluorescent amino compound (9-aminofluorene) to form phenylthiocarbamyl amino acid derivatives, and the products were detected with high sensitivity.

A similar procedure to that described in Example 1 was followed till a step of obtaining anilino thiazolinone derivatives. The anilino thiazolinone derivative of leucine (hereinafter abbreviated as ATZ-Leu) was used.

This reaction proceeded according to the following reaction formula to form a phenylthiocarbamyl amino acid derivative.

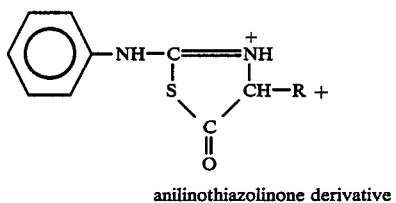

anilinothiazolinone derivative

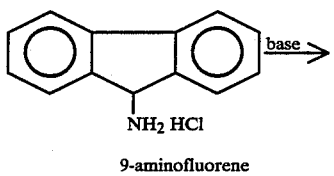

9-aminofluorene

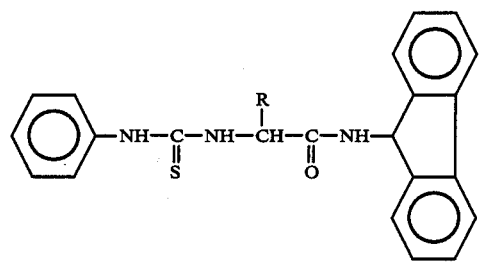

R:Leu phenylthiocarbamyl amino acid derivative

The reaction was performed in the following way. To ATZ-Leu (70 mg, 0.21 mM) was added 9-aminofluorene (130 mg, 0.6 mM) dissolved in 30% pyridine-dimethylformamide, and the resulting mixture was reacted by heating at 50° C. for one hour.

After the reaction, the reaction solution was evaporated to dryness. CHCl$_3$ was added to the residue and the insoluble matter (9-aminofluorene.HCl) was separated by filtration. The CHCl$_3$ was washed with 0.1N HCl and 0.11N NaHCO$_3$, over Na$_2$SO$_4$ and concentrated to dryness. The residue was recrystallized from benzene to obtain a product in the form of a white crystal.

Yield: 130 mg, % yield: 88%, m.p.: 225° C.

Figure 5:
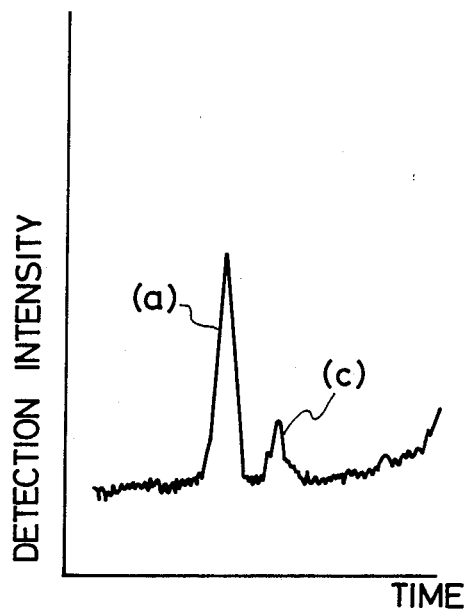
FIG. 5 are HPLC charts of a reaction mixture and a reaction product (mixing or reaction between ATZ-Leu and aminofluorene)
Figure 5:
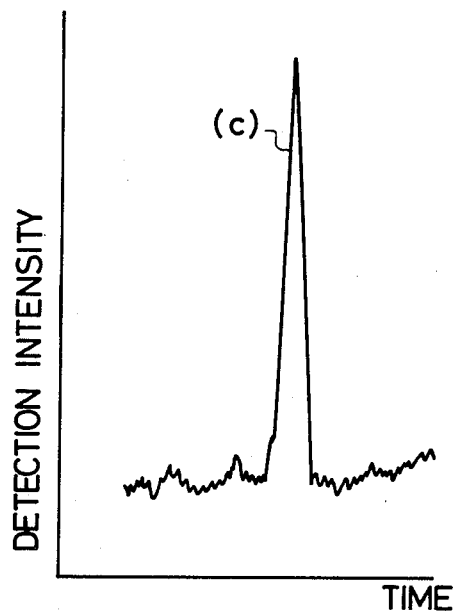

Each of the reaction mixture and the reaction product was passed through a high-pressure liquid chromatography (HPLC) column, and the detection was performed by ultraviolet fluorescence spectra (at 269 nm). The results are shown in FIG. 5. FIG. 5 (i) shows an HPLC chart of the reaction mixture just after mixing, and FIG. 5 (ii) shows an chromatogram chart after reacting by heating at 50° C. for one hour. As these figures clearly show, anilinothiazolinone derivative (a) of leucine after the reaction was detected in the form of a phenylthiocarbamyl leucine derivative (c). In addition, a comparison of the sensitivity of detection between the method this invention and of the prior art phenylthiohydantoin amino acid detection method revealed that the former was extremely high as follows:

| detection method | sensitiviy of detection |
|---|---|
| Phenylthiohydantoin amino acid method (prior art) | ~10 pico mole |
| this invention | 0.1 ~ 1 pico mole |

Extremely high sensitivity of detection of the amino acid derivatives of this invention is shown below by comparison with the sensitivity of detection in the prior art method in which a phenylthiocarbamyl amino acid derivative (phenylthiohydantoin amino acid) is used:

| detection method | sensitivity of detection |
|---|---|
| phenylthiohydantoin amino acid detection method (prior art) | 1 ~ 10 pico mole |
| this invention: when iodine isotope labelling is used | 1 ~ 10 femto mole |
| when a fluorescent amino compound is used | 0.1 ~ 1 pico mole. |

The gist of this invention resides in reacting an iodine-labelled amine compound or a fluorescent amino compound with a thiazolinone derivative of an amino acid to form a phenylthiocarbamyl amino acid derivative and detecting it with high sensitivity. Although only those examples in which iodohistamine or aminofluorene was used were shown above, it is apparent that the effect of this invention can be attained by using other iodine-labelled or fluorescent amino compounds and is not limited to particular examples. Therefore, the detection method for amino acids of this invention is of great industrial value.

What is claimed is:

1. A method for detecting 5-thiazolinone derivatives of amino acids comprising:

reacting (a) 5-thiazolinone derivatives of amino acids with (b) an amino compound labeled with a radioactive isotope to form (c) phenylthiocarbamyl amino acid derivatives according to the reaction scheme:

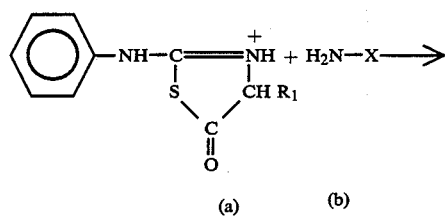

(a)  (b)

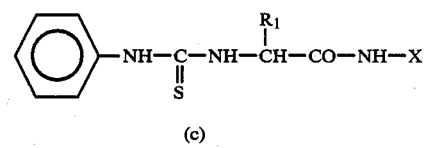

(c)

wherein X is a residue of a radioactive isotope label and R$_1$ is hydrogen or a hydrocarbon radical; and detecting the phenylthiocarbamyl amino acid derivatives.

2. A method of detecting amino acids comprising:
reacting (d) phenylisothiocyanate with (e) a protein or peptide to form (f) phenylthiocarbamyl protein;
reacting the (f) phenylthiocarbamyl protein with (g) an acid in an anhydrous condition to effect cyclization and scission and to form (a) a 5-thiazolinone derivative; and
reacting the (a) 5-thiazolinone derivative with (b) an amino compound labeled with a radioactive isotope to form (c) phenylthiocarbamyl amino acid derivatives according to the reaction scheme:

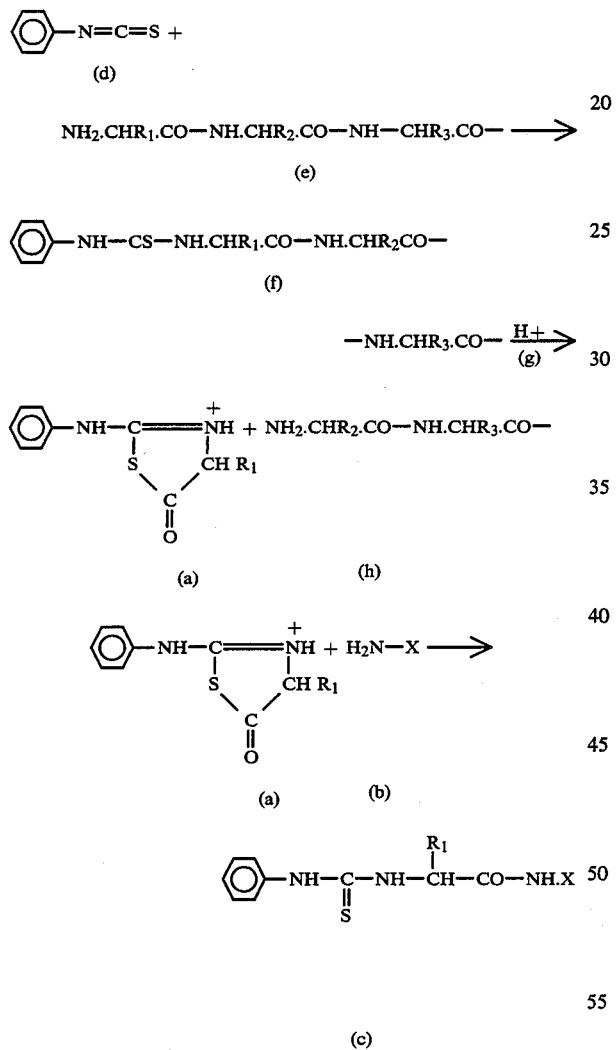

wherein each of $R_1$, $R_2$, and $R_3$ is hydrogen or a hydrocarbon radical, X is a residue of radioactive isotope label, and wherein (h) is the cleaved peptide or protein.

3. A method for detecting 5-thiazolinone derivatives of amino acids comprising:
reacting (a) 5-thiazolinone derivatives of amino acids with (b) a fluorescent amino compound to form (c) phenylthiocarbamyl amino acid derivatives according to the reaction scheme:

wherein X is a fluorescent compound and $R_1$ is hydrogen or a hydrocarbon radical.

4. A method of detecting amino acids comprising:
reacting (d) phenylisothiocyanate with (e) a protein or peptide to form (f) phenylthiocarbamyl amino;
reacting the (f) phenylthiocarbamyl protein with (g) an acid in an anhydrous condition to effect cyclization and scission and to form (a) a 5-thiazolinone derivative; and
reacting the (a) 5-thiazolinone derivative with (b) a fluorescent amino compound to form (c) phenylthiocarbamylamino acid derivatives according to the reaction scheme:

-continued

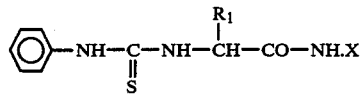

(c)

wherein each of $R_1$, $R_2$, $R_3$ is hydrogen or a hydrocarbon radycal, X is a fluorescent compound, and wherein (h) is the cleaved peptide or protein.

5. A method for detecting 5-thiazolinone derivatives of amino acids comprising:

reacting (a) 5-thiazolinone derivatives of amino acids with (b) an amino compound labeled with a radioactive isotope to form (c) phenylthiocarbamyl amino acid derivatives according to the reaction scheme:

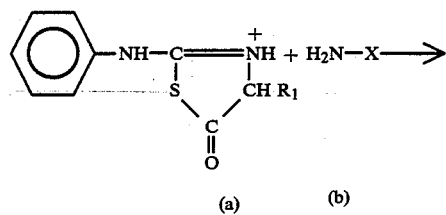

(a)    (b)

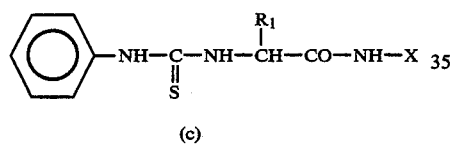

(c)

wherein X is a residue of a radioactive isotope label and $R_1$ is an amino acid side chain; and detecting the phenylthiocarbamyl amino acid derivatives.

6. A method of detecting amino acids comprising:

reacting (d) phenylisothiocyanate with (e) a protein or peptide to form (f) phenylthiocarbamyl protein;

reacting the (f) phenylthiocarbamyl protein with (g) an acid in an anhydrous condition to effect cyclization and scission and to form (a) a 5-thiazolinone derivative; and reacting the (a) 5-thiazolinone derivative with (b) an amino compound labeled with a radioactive isotope to form (c) phenylthiocarbamyl amino acid derivatives according to the reaction scheme:

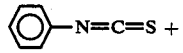

(d)

$NH_2.CHR_1.CO\text{—}NH.CHR_2.CO\text{—}NH\text{—}CHR_3.CO\text{—} \longrightarrow$ (e)

(f)

$-NH.CHR_3.CO\text{—} \xrightarrow{H+}$ (g)

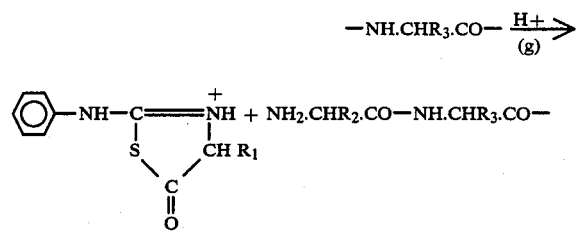

(a)    (h)

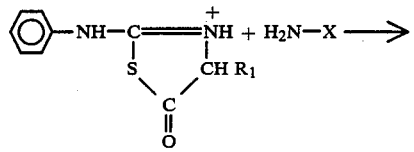

(a)    (b)

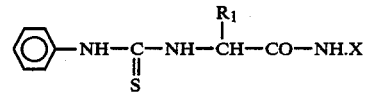

(c)

wherein each of $R_1$, $R_2$, and $R_3$ is an amino acid side chain, X is a residue of a radioactive isotope label, and wherein (h) is the cleaved peptide or protein.

7. A method for detecting 5-thiazolinone derivatives of amino acids comprising:

reacting (a) 5-thiazolinone derivatives of amino acids with (b) a fluorescent amino compound to form (c) phenylthiocarbamyl amino acid derivatives according to the reaction scheme:

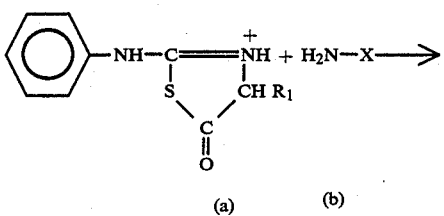

(a)    (b)

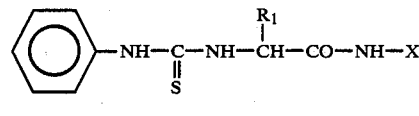

(c)

wherein X is a fluorescent compound and $R_1$ is an amino acid side chain.

8. A method of detecting amino acids comprising:

reacting (d) phenylisothiocyanate with (e) a protein or peptide to form (f) phenylthiocarbamyl protein;

reacting the (f) phenylthiocarbamyl protein with (g) an acid in an anhydrous condition to effect cyclization and scission and to form (a) a 5-thiazolinone derivative; and reacting the (a) 5-thiazolinone derivative with (b) a fluorescent amino compound to form (c) phenylthiocarbamyl amino acid derivatives according to the reaction scheme:
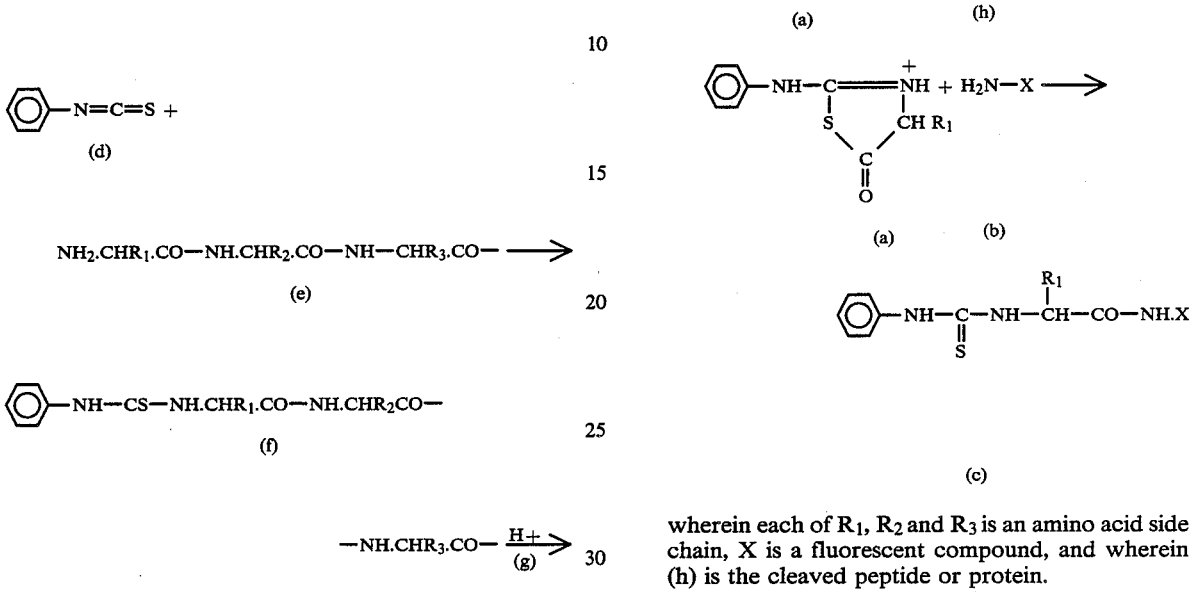
wherein each of $R_1$, $R_2$ and $R_3$ is an amino acid side chain, X is a fluorescent compound, and wherein (h) is the cleaved peptide or protein.
* * * * *